United States Patent
Brunswick et al.

(10) Patent No.: US 8,934,954 B2
(45) Date of Patent: Jan. 13, 2015

(54) ASSESSMENT OF SUDOMOR FUNCTION FOR PERIPHERAL DIABETIC NEUROPATHY EVALUATION

(75) Inventors: Philippe Brunswick, Paris (FR); Kamel Khalfallah, Paris (FR); Jean Henry Calvet, Paris (FR)

(73) Assignee: Impeto Medical, Paris (FR)

( * ) Notice: Subject to any disclaimer, the term of this patent is extended or adjusted under 35 U.S.C. 154(b) by 372 days.

(21) Appl. No.: 13/215,813

(22) Filed: Aug. 23, 2011

(65) Prior Publication Data
US 2013/0053721 A1   Feb. 28, 2013

(51) Int. Cl.
*A61B 5/05*  (2006.01)
*A61B 5/00*  (2006.01)
*A61B 5/053* (2006.01)

(52) U.S. Cl.
CPC .............. *A61B 5/0531* (2013.01); *A61B 5/4076* (2013.01)
USPC .......................................... 600/346; 600/554

(58) Field of Classification Search
USPC .......................... 600/345, 346, 547, 554, 573
See application file for complete search history.

(56) References Cited

U.S. PATENT DOCUMENTS

| | | |
|---|---|---|
| 3,821,949 A | 7/1974 | Hartzell et al. |
| 4,365,637 A | 12/1982 | Johnson |
| 4,509,531 A | 4/1985 | Ward |
| 4,690,152 A | 9/1987 | Juncosa |
| 4,794,934 A | 1/1989 | Motoyama et al. |
| 5,307,817 A | 5/1994 | Guggenbuhl et al. |
| 5,406,956 A | 4/1995 | Farwell |
| 5,771,261 A | 6/1998 | Anbar |
| 5,782,884 A | 7/1998 | Stotts et al. |
| 5,800,350 A | 9/1998 | Coppleson et al. |

(Continued)

FOREIGN PATENT DOCUMENTS

| | | |
|---|---|---|
| WO | WO-00/19894 A1 | 4/2000 |
| WO | WO-2006/136598 A2 | 12/2006 |
| WO | WO-2011/070422 A1 | 6/2011 |

OTHER PUBLICATIONS

Kamel Khalfallah et al: "Noninvasive Galvanic Skin Sensor for Early Diagnosis of Sudomotor Dysfunction: Application to Diabetes", IEEE Sensors Journal, IEEE Service Center, New York, NY, Dec. 30, 2010.*

(Continued)

*Primary Examiner* — Max Hindenburg
*Assistant Examiner* — Jonathan M Foreman
(74) *Attorney, Agent, or Firm* — Harness, Dickey & Pierce, P.L.C.

(57) ABSTRACT

A method for assessing sudomotor function of a patient for evaluating diabetic and autonomous neuropathy is disclosed. The method is performed in a system comprising electrodes intended to be placed on different regions of the patient body, and an adjustable DC source. The method includes applying on the electrodes DC voltage pulses of varying voltage values in order to stress sweat glands, the voltage pulses lasting given durations allowing the stabilization of electrochemical phenomena in the body, near the electrodes; collecting data representative of the current between the electrodes, and of the potential generated on the electrodes for the different DC voltages; from the data, computing results representative of the electrochemical skin conductance of the patient; reconciling the latter data with reference data obtained in the same conditions on patients identified as suffering or not from sudomotor, and identifying the patient as suffering or not from sudomotor dysfunction.

14 Claims, 5 Drawing Sheets

(56) References Cited

U.S. PATENT DOCUMENTS

| | | | |
|---|---|---|---|
| 5,928,155 | A | 7/1999 | Eggers et al. |
| 6,175,752 | B1 | 1/2001 | Say et al. |
| 6,299,583 | B1 | 10/2001 | Eggers et al. |
| 6,336,045 | B1 | 1/2002 | Brooks |
| 6,473,641 | B1 | 10/2002 | Kodama et al. |
| 6,491,647 | B1 | 12/2002 | Bridger et al. |
| 6,512,949 | B1 | 1/2003 | Combs et al. |
| 6,577,893 | B1 | 6/2003 | Besson et al. |
| 6,871,084 | B1 | 3/2005 | Kingsley et al. |
| 7,161,362 | B2 | 1/2007 | Shambroom et al. |
| 7,477,937 | B2 | 1/2009 | Iijima et al. |
| 7,931,592 | B2 | 4/2011 | Currie et al. |
| 8,085,144 | B2 | 12/2011 | Appelt et al. |
| 2002/0107452 | A1 | 8/2002 | Kwong |
| 2004/0128088 | A1 | 7/2004 | Laletin et al. |
| 2005/0113650 | A1 | 5/2005 | Pacione et al. |
| 2005/0245839 | A1 | 11/2005 | Stivoric et al. |
| 2006/0085049 | A1 | 4/2006 | Cory et al. |
| 2006/0127964 | A1 | 6/2006 | Ford et al. |
| 2007/0124176 | A1 | 5/2007 | Jung et al. |
| 2007/0178167 | A1 | 8/2007 | Andrijauskas |
| 2009/0054742 | A1 | 2/2009 | Kaminska et al. |
| 2009/0318779 | A1 | 12/2009 | Tran |
| 2009/0326407 | A1 | 12/2009 | Tournefier et al. |
| 2010/0081941 | A1 | 4/2010 | Naghavi et al. |

OTHER PUBLICATIONS

Hubert, D. et al.; "Abnormal electrochemical skin conductance in cystic fibrosis"; Journal of Cystic Fibrosis; Feb. 24, 2010; 6 pages.

Mayaudon, H. et al.; "A new simple method for assessing sudomotor function: Relevance in type 2 diabetes"; Diabetes & Metabolism 36 (2010); Mar. 31, 2010; pp. 450-454.

Millasseau, Sandrine C. et al.; "Contour analysis of the photoplethysmographic pulse measured at the finger," Journal of Hypertension, vol. 24, No. 8, Aug. 2006, pp. 1449-1456.

Allen, John: "Topical Review; Photoplethysmography and its application in clinical physiological measurement," IOP Publishing, vol. 28, No. 3. Mar. 1, 2007, pp. R1-R39.

Li, Jin et al; "Computation of Cardiac Output by Pulse Wave Contour," IEEE, 2007, pp. 1088-1090.

Awad, Aymen A. et al.; "The Relationship Between the Photoplethysmographic Waveform and Systemic Vascular Resistance," Journal of Clinical Monitoring and Computing, vol. 21, No. 6, Oct. 17, 2007, pp. 365-372.

Wang, L. et al.; "Noninvasive Cardiac Output Estimation Using a Novel Photoplethysmogram Index," 31st Annual International Conference of the IEEE EMBS, Minneapolis, MN, Sep. 2-6, 2009, pp. 1746-1749.

* cited by examiner

FIG. 4

|  | ESC >60(μS) | ESC 40-60(μS) | ESC <40(μS) | p-value |
|---|---|---|---|---|
| N | 130 | 67 | 68 |  |
| Men [n (%)] | 74 (57%) | 38 (56%) | 37 (54%) |  |
| Age (yrs) | 51.0 (11.5) | 53.0 (11.5) | 57.0 (10E5) |  |
| Duration of DM (yrs) | 6.0 (10.0) | 8.0 (10.0) | 12.5 (10E5) | 0.00 |
| BMI (kg/(m)$^2$) | 25.9 (5.1) | 26.7 (5.2) | 26.3 (5.3) | 0.88 |
| Waist Hip Ratio | 0.95 (0.09) | 0.96 (0.11) | 0.96 (0.11) | 0.43 |
| Random Glucose (mg%) | 169.0 (89.7) | 171.0 (99.5) | 159.0 (106.7) | 0.76 |
| HbAlc (%) | 8.0 (2.0) | 8.3 (2.6) | 8.6 (2.7) | 0.00 |
| Hemoglobin (g%) | 12.5 (2.3) | 12.5 (1.9) | 12.1 (2.3) | 0.00 |
| B12 (pmol/L) | 199.5 (153.7) | 220.0 (216.0) | 289.0 (228.7) | 0.03 |
| Folic Acid (nmol/L) | 18.0 (23.8) | 19.8 (23.8) | 21.7 (33.4) | 0.26 |
| Creatinine (mg%) | 0.7 (0.3) | 0.7 (0.2) | 0.8 (0.3) | 0.47 |
| eGFR (ml/min/l.73m2) | 111.0 (34.9) | 110.0 (38.3) | 97.2 (32.0) | 0.10 |
| VPT (Volts) | 11.5 (7.0) | 13.0 (6.5) | 15.0 (12.2) | 0.00 |
| MNSI B score >2 [n (%)1] | 59 (45%) | 38 (56%) | 47 (69%) | 0.00 |
| Patients with all Ewing tests performed (N=171) | 87 | 52 | 32 |  |
| >= 2 Abnormal Ewing test [n (%)] | 9 (10%) | 4 (8%) | 10 (31%) | 0.01 |

FIG. 5a

|  | Normal<br>MNSI B score ≤ 2<br>(N=121) | Severe<br>MNSI B score > 2<br>(N=144) | P-value |
|---|---|---|---|
| Gender | M (74), F (47) | M (75), F (69) |  |
| Age (yrs) | 51.0 (11.0) | 56.0 (11.2) | 0.00 |
| Duration of DM (yrs) | 5.00 (10.0) | 11.0 (11.0) | 0.00 |
| BMI (kg/(m)$^2$) | 25.0 (4.8) | 26.7 (4.9) | 0.03 |
| Waist-Hip Ratio | 0.96 (0.09) | 0.95 (0.12) | 0.76 |
| Random Glucose (mg%) | 165.0 (85.0) | 169.0 (106.7) | 0.95 |
| HbA1C (%) | 8.0 (2.3) | 8.4 (2.4) | 0.15 |
| Vit. B12 (pmol/L) | 184.0 (186.0) | 238.0 (216.5) | 0.00 |
| Folic Acid (nmol/L) | 8.0 (21.8) | 20.3 (26.0) | 0.39 |
| Creatinine (mg%) | 0.7 (0.3) | 0.7 (0.3) | 0.79 |
| eGFR (ml/min/1.73m2) | 110.4 (39.7) | 106.7 (32.3) | 0.22 |
| Hemoglobin (gm%) | 12.7 (2.2) | 12.1 (2.0) | 0.00 |
| Hand ESC (μS) | 60.0 (27.5) | 49.0 (33.2) | 0.00 |
| Feet ESC (μS) | 62.0 (26.0) | 47.2 (33.0) | 0.00 |
| VPT (volts) | 9.0 (5.0) | 15.0 (7.6) | 0.00 |

FIG. 5b

| | Normal VPT ≤10V (N=90) | Mild VPT >10 - 15 V (N=93) | Moderate VPT >15 - 25 V (N=60) | Severe VPT >25 V (n=22) | P-value |
|---|---|---|---|---|---|
| Gender | M(45) ; F(45) | M(52) ; F(41) | M(35) ; F(25) | M(17) ; F (5) | |
| Age (yrs) | 49.0 (10.0) | 53.0 (12.0) | 56.5 (8.2) | 61.5 (8.5) | 0.00 |
| Duration of DM (yrs) | 4.5 (8.7) | 8.0 (8.0) | 12.0 (10.0) | 16.0 (8.0) | 0.00 |
| BMI (kg/(m)2) | 25.9 (4.9) | 26.5 (5.5) | 26.2 (5.4) | 25.9 (3.8) | 0.85 |
| Waist-Hip Ratio | 0.94 (0.07) | 0.95 (0.13) | 0.98 (0.11) | 0.99 (0.10) | 0.01 |
| Random Glucose (mg%) | 162.5 (89.0) | 161.0 (78.0) | 175.5 (102.0) | 186.5 (134.5) | 0.43 |
| HbA1C (%) | 7.8 (2.0) | 8.0 (2.3) | 8.8 (2.1) | 8.8 (2.4) | 0.01 |
| Vit. B12 (pmol/L) | 185.0 (187.5) | 207.0 (164.0) | 236.0 (326.2) | 348.5 (291.2) | 0.00 |
| Folic Acid (nmol/L) | 19.8 (25.4) | 17.9 (16.2) | 22.6 (26.2) | 19.1 (51.1) | 0.87 |
| Creatinine (mg%) | 0.7 (0.2) | 0.7 (0.2) | 0.8 (0.3) | 0.9 (0.3) | 0.02 |
| eGFR (ml/min/1.73m2) | 111.8 (35.7) | 111.8 (38.7) | 106.0 (26.0) | 92.1 (34.3) | 0.01 |
| Hemoglobin (gm%) | 12.3 (2.4) | 12.5 (2.3) | 12.3 (2.0) | 12.1 (2.7) | 0.65 |
| Hand ESC (μS) | 60.2 (26.3) | 55.0 (30.5) | 57.7 (36.1) | 42.7 (28.6) | 0.00 |
| Feet ESC (μS) | 61.0 (26.8) | 61.0 (28.5) | 48.2 (35.5) | 38.2 (45.0) | 0.01 |
| Mich B> 2 | 15 (16%) | 62 (66%) | 47 (78%) | 20 (90%) | 0.00 |

ASSESSMENT OF SUDOMOR FUNCTION FOR PERIPHERAL DIABETIC NEUROPATHY EVALUATION

BACKGROUND OF THE INVENTION

1. Field

The invention relates in general to medical diagnostic devices and methods in the field of human health. The invention more specifically applies to diagnostic of autonomic neuropathy, and in particular to diabetic polyneuropathy.

2. Description of the Related Art

Diabetic polyneuropathy (DPN) is partly a peripheral autonomic neuropathy (PAN) that is linked to lesions of small unmyelinated fibres. These unmyelinated fibers, including those that innervate the sweat glands, are the first to undergo damage. As such, DPN is a nerve-length-dependent process that firstly affects the feet.

Peripheral autonomic neuropathy (PAN) results in the atrophy of sweat glands and decreased sudomotor response that may affect the skin suppleness and flexibility that prevent skin cracks and ulceration, and may also reduce sweating, leading to abnormal skin conditions such as dryness, fissures and blisters.

Moreover, PAN results in decreased foot sensitivity. The prevalence of PAN has recently been estimated to affect 43% of diabetic patients aged 40-70 years. Early detection of symmetrical distal sensory—motor DPN can decrease morbidity and the risk of foot complications.

Sensory function is considered one of the major initiating risk factors in the pathogenesis of diabetic foot ulcer. As no gold standard is available for early diagnosis of DPN, vibration perception threshold (VPT), using a biothesiometer, and pressure perception, using Semmes-Weinstein monofilaments, have been proposed to identify patients at risk, but none of these investigates peripheral autonomic involvement.

Peripheral autonomic neuropathies such as DPN are also usually evaluated through sudomotor function, using the sympathetic skin response (SSR), or by quantitative sudomotor axon reflex testing (QSART). These methods require specialized training to perform and are also time-consuming procedures. Neuropad® is another alternative test targeted for use by the patient, although it is less sensitive and semi-quantitative.

Thus, the need for highly trained personnel, lack of sensitivity, non-quantitative results and time required to take measurements have restricted the widespread use of sudomotor function assessment in clinical practice. There is therefore a need for an alternative method for detecting peripheral autonomic neuropathies such as diabetic polyneuropathy through assessment of sudomotor function.

SUMMARY OF THE INVENTION

Thus, the object of the present invention is to provide a new method for quickly assessing sudomotor function of a patient through electrochemical skin conductance (ESC) evaluation. Another objet of the invention is to provide a non-invasive and quantitative measurement that is easy to implement on a patient.

According to the invention, a method for diagnosing a patient, by assessment of sudomotor function based on ESC evaluation through reverse iontophoresis is provided. In a preferred embodiment, the method is performed in a system comprising an anode and a cathode, intended to be placed on different regions of the patient body, and an adjustable DC source, which is controlled in order to feed the anode with a DC current, and comprises the step consisting of:

applying DC voltage pulses of varying voltage values in order to stress sweat glands, the voltage pulses lasting given durations allowing the stabilization of electrochemical phenomena in the body in the vicinity of the electrodes, collecting data representative of the current between the anode and the cathode, and of the potential generated on the cathode through reverse iontophoresis for the different DC voltages, from said data, computing results representative of the electrochemical skin conductance of the patient, reconciling said data representative of the electrochemical skin conductance of the patient with reference data obtained in the same conditions on patients identified as suffering or not from autonomic neuropathy, and identifying the patient as suffering or not from sudomotor dysfunction.

The computation step may comprise the computation of electrochemical skin conductance values at given voltages, by computing the ratio between the current generated through the anode and the cathode, and the resulting voltage drop between anode and cathode. In some embodiments, the patient is identified as suffering from diabetes, and the reconciliation step allows identifying the patient as suffering or not from diabetes polyneuropathy.

The method may further comprise at least one test among the following: peripheral vibration sensation through evaluation of the vibration perception threshold, cardiac autonomic neuropathy (CAN) assessment, neuropathy assessment through Michigan neuropathy screening instrument (MNSI).

BRIEF DESCRIPTION OF THE DRAWINGS

The features and advantages of the invention will be apparent from the following more detailed description of certain embodiments of the invention and as illustrated in the accompanying drawings, in which:

FIG. 4 shows the results of statistical analyses carried out with the method according to the invention.

FIG. 5a shows comparison of clinical, biochemical characteristics and conductance measurement in patients with clinical neuropathy according to MNSI B score.

FIG. 5b shows comparison of clinical, biochemical characteristics and conductance measurement in patients with increasing vibration perception threshold.

DETAILED DESCRIPTION OF A PREFERRED EMBODIMENT

Description of a Diagnosis System According to the Invention

Figure 1:
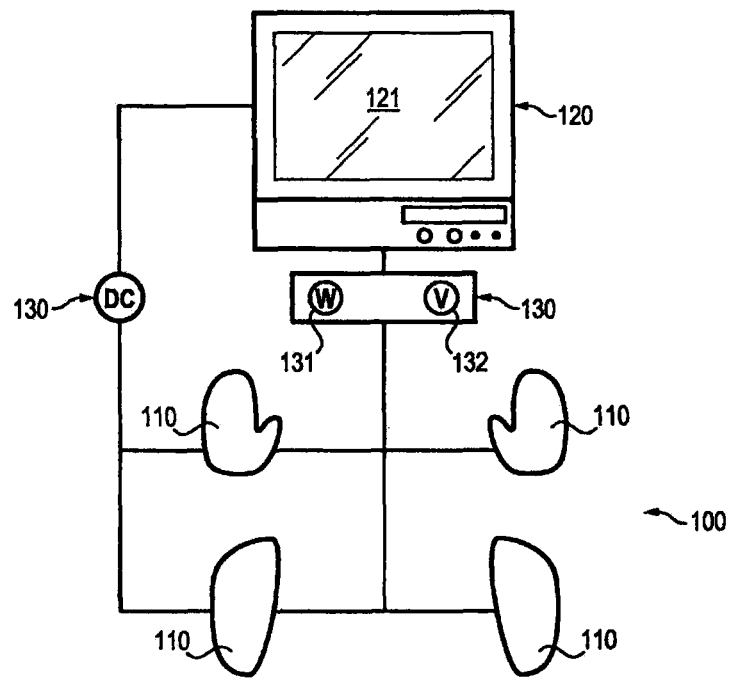
FIG. 1 shows a system for designed to carry out the method according to the invention.

A system 100 for assessing the sudomotor function of a patient through reverse iontophoresis is shown on FIG. 1. The system 100 comprises a series of large area electrodes 110, preferably four electrodes 110, on which the patient can place his hands and feet. The sites of the electrodes 110 have been chosen because of their high density of eccrine sweat glands.

The electrodes 110 can be made of nickel or stainless steel with sufficient level of nickel. Their individual surface area is comprised between 50 cm² and 200 cm², so that they cover substantially all the surface of the hand palms and of the feet soles. Yet they can be adapted for children or even infants.

They are connected to a computer 120 for collecting, computing, and storing data. They are also connected to an adjustable DC source 130, which is controlled by an operator or the computer 120 to feed the electrodes 110 with a DC current of a determined voltage. The system 100 also comprises a measuring circuit 130, to measure the voltage potential of each electrode through a voltmeter 131, as well as the current between two electrodes through a Wheatstone bridge 132. The diagnosing system can also be equipped with a display 121, designed for displaying the measured data as well as the results of the computations carried out on said data.

Figure 2:
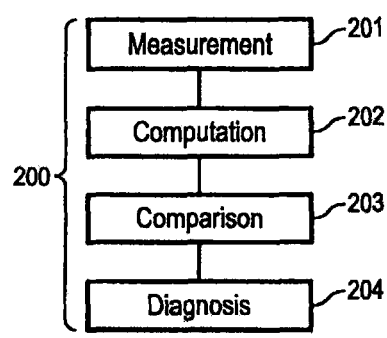
FIG. 2 shows the main steps carried out in the diagnosis method according to the invention.

The diagnosis method 200 according to the invention will now be described in reference to FIG. 2.

Measurement Step 201

In order to assess sudomotor function of a patient, in view of detecting autonomic neuropathy, the patient places his/her hands and/or feet on the large area nickel electrodes 110, and stands up without moving his hands and/or feet during the 2 minutes that lasts the measurement. At the low DC voltages applied to the skin, typically less than 10 V, the outermost layer of the skin, called Stratum Corneum (SC), is electrically insulating and only the appendageal pathway is conductive, so that only the eccrine sweat glands are stressed. The fact that these glands are the most numerous and present at almost all parts of the skin, and in abundance (500 per cm2) at hand palm and foot sole, allows an effective electrical response of the skin.

For the measurement 201, the electrodes are used alternatively as an anode and as a cathode and a DC incremental voltage <10 V is applied at anode. Up to twenty pulses are applied, each of duration between 0.5 s and 1 s, which allows the stabilisation of electrochemical phenomena towards steady states in the body, in the vicinity of the electrodes. The pulse voltages are increased and/or decreased between for example 1 V and 4 V approximately.

The electrochemical phenomena are measured by two active electrodes (the anode and the cathode) successively and independently for the two feet and for the two hands. The two other passive electrodes allow retrieval of the potential reached by the body. The applied voltage on the anode induces, through reverse iontophoresis, a voltage on the cathode and generates a current (intensity of around 0.2 mA). It is carried across the gland by chloride and proton, is going through the body between anode and cathode and is directly related to ESC.

Figure 3:
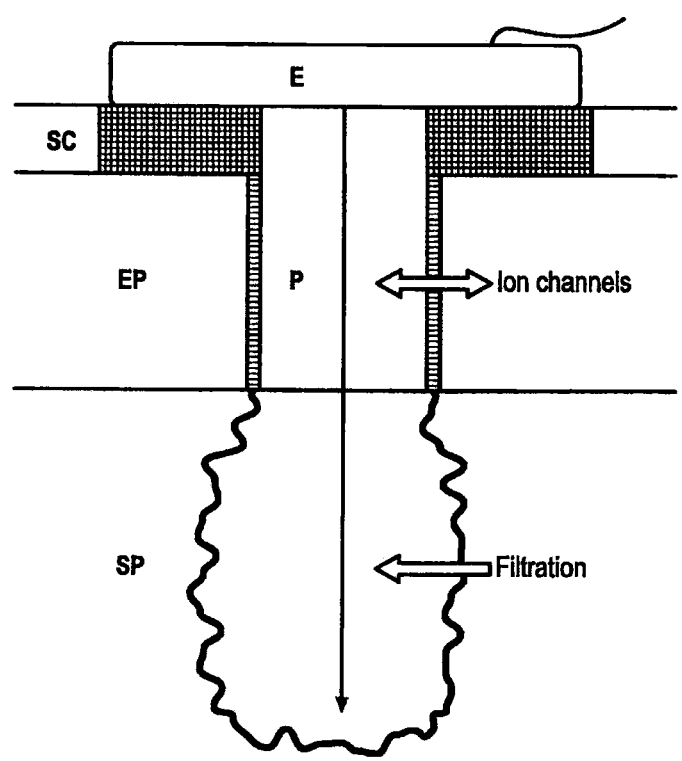
FIG. 3 is a schematic representation of an eccrine gland that transport the DC current in the electrolyte (sweat), with chloride at anode and proton at cathode.

FIG. 3 is a schematic view of an eccrine gland stressed by an electrode E. An eccrine gland comprises the secretory part SP, where the sweat is filtered from blood plasma in a coil, and the excretory part EP, where some species can move in both sides (entry or absorption according to their electrochemical gradient) across some ionic channels in a duct almost straight that leads to a pore P on the skin surface. The Stratum Corneum SC is represented on the skin surface.

ESC is neither influenced by the Stratum Corneum thickness, nor the sweat conductivity. It is the lateral surface conductance of the wall of the gland which is measured. As chloride is produced by sweat glands, when the latter is stressed by the electric field created by the electrodes, the current generated between the electrodes is representative of the sudomotor function which is impaired by peripheral autonomic neuropathies such as diabetic polyneuropathy.

The measurement of the current through the electrodes and voltages of active and passive electrodes thus allows assessing the sudomotor function of the sweat glands. Both electrodes voltages and current between them are measured and stored by the computer 120 at measurement step 201. The same series of measurements can then be carried out with the electrodes being reversed (anode becoming cathode and vice-versa), and the same can be carried out on the feet/hands.

Computation 202

Once the electrodes potentials have been recorded, the computer 120 determines the electrical skin conductance (ESC) of the patient by calculating the ratio between the current generated through the active electrodes and the resulting voltage drop between anode and cathode. The electrical skin conductance can be plotted for each voltage value applied to the anode. In that case, the plot can be displayed on the display 121.

Comparison with Healthy Patients 203

ESC values are then compared to traditional tests results for assessing autonomic neuropathies, in order to check the indications given by the ESC results. A large-scale experiment was carried out on 265 consecutive diabetic patients, by implementing on them the method according to the invention, as well as traditional tests such as Ewing's cardiac autonomic function tests and Heart Rate Variability analysis (HRV), vibration perception threshold measurement (VPT), and neuropathy assessment using the Michigan Neuropathy Screening Instrument (MNSI).

Patients were accepted on the condition of having had a diagnosis of type 2 diabetes. Exclusion criteria were patients taking drugs that would have an effect on the sympathetic system such as beta blocker, amputation of arms or legs, electrical implantable device (pacemaker/defibrillator), sensitivity to nickel or any other standard electrodes, suffering from seizures, epilepsy or proliferative retinopathy, suffered Myocardial infarction (MI) and/or stroke in the past 6 months, arrhythmia's, treatment with anti-arrhythmic drugs and any advanced systemic condition.

Ewing's cardiac autonomic function tests comprise four tests. Each test was carried out according to the standard procedure described by Ewing et al in:

"Diagnosis and management of diabetic autonomic neuropathy" (Ewing D J, Clarke B F, Br Med J 1982; 285:916-918)

HRV during deep breathing test (E/I ratio): R-R intervals during inhalation and exhalation are calculated. The longest R-R interval is determined during expiration (R-R max) and the shortest interval during inspiration (R-R min). The result is then expressed as the ratio of the heart rate at expiration to that at inspiration and is called as E/I ratio. Normal values are superior to 1.21.

HRV during standing test (30/15 ratio): shortest R-R interval is measured after standing when heart rate is maximum, which is around the $15^{th}$ beat. This is followed by bradycardia which is indicated by the longest R-R interval around $30^{th}$ beat. The ratio of longest to shortest R-R is calculated which is also called as 30/15 ratio. Normal values are superior to 1.03.

HRV during Valsalva maneuver test: the heart rate rises during the maneuver and after the maneuver the heart rate slows. In this test the ratio of longest r-R interval after maneuver to shortest R-R interval during the maneuver is calculated. Normal values are superior to 1.20.

Blood pressure response to standing (Orthostatic Blood Pressure Response): the postural fall in the blood pressure is taken as the difference between the systolic blood pressure lying and standing. Normal fall is inferior to 20 mmHg.

An abnormality in at least two tests is required to ensure the diagnosis of Cardiac Autonomic Neuropathy (CAN). Vibration Perception Threshold (VPT) was measured on both sides using a biothesiometer on the plantar side of the great toe on a continuous scale. The mean between the two sides was used for analysis. Four groups were then defined: VPT<10 V: no neuropathy, VPT between 10 and 15 V: mild neuropathy, VPT between 15 and 25 V: moderate neuropathy, and VPT superior to 25 V: severe neuropathy.

The neuropathy assessment through use of Michigan neuropathy Screening Instrument (MNSI) was implemented with both a questionnaire to record neuropathic symptoms (MNSI A), and clinical assessment, including foot inspection (deformities, skin changes and infection), ankle reflex testing, vibration sensation using 128 Hz tuning fork and touch sensation perception using 10-g Semmes-Weinstein monofilament (MNSI B). Biochemical analyses were also performed.

Non-fasting blood sample was collected in EDTA vacutainer, and processed to obtain plasma. Plasma aliquots were stored (−70° C.) until further analysis. Hemoglobin was measured on whole blood on a Beckman Coulter Analyzer (AC.T diff™, Miami, Fla., USA). Plasma glucose, uric acid, creatinine, Gamma-GT, SGPT and SGOT and urine creatinine were measured on an automated biochemistry analyzer (Hitachi 902, Germany), using standard enzymatic methods. HbA1c was measured using HPLC method on BioRad-D10 (US) Plasma B12 and folate were measured by microbiological assays. Urine albumin was measured using an immunoprecipitation assay and albumin-creatinine ratio was calculated.

The results of this experiment, which are discussed hereinafter, are shown on FIG. 4, FIG. 5a and FIG. 5b. FIG. 4 shows clinical characteristics of the patients and their biothesiometer reading and CAN results by categories of decreasing feet ESC distribution. P-values are calculated using Simple Linear Regression Analysis for continuous variables and Chi square proportion trend test for categorical variables.

FIG. 5a shows clinical, biochemical characteristics and hands and feet ESC values in patients with and without clinical neuropathy. P-values were calculated using Kruskal-Wallis test for continuous variables.

FIG. 5b shows Clinical, biochemical characteristics and hands and feet ESC values in patients with increasing degrees of VPT. P-values were calculated using Kruskal-wallis test for continuous variables and chi-square trend test for categorical variables.

Data are presented as median (25th-75th percentile). Normality of the variables was checked and appropriate transformations were done. Following variables needed transformation: Log transformation for Folic Acid, Biothesiometer, Maximum/Minimum 30/15 Ratio and Valsalva maneuver, log-log transformation for B12 and E/I Ratio, and square root transformation for Michigan Score A. Agreement between left and right electrode readings for different sites was investigated using mean percent difference and Coefficient of Variation (CV). Simple linear regression analysis was used to study the association of hands and feet ESC with continuous measurements such as biothesiometer, MNSI and CAN. Agreement between biothesiometer readings, MNSI score and feet ESC values was studied using simple linear regression analysis with prediction interval by calculating percentage of observation outside the prediction limit.

Low percentage indicates good agreement. Independent biological determinants were tested using multiple linear regression analysis. Area under the curve (AUC) of the ROC curve was calculated to measure the efficiency of feet ESC in diagnosing patients with and without neuropathy based on VPT value.

As visible on FIG. 4, lower ESC reading was significantly associated with higher age, longer duration of DM, higher HbA1c, lower hemoglobin and higher plasma vitamin B12 concentration. There was no difference between men and women. BMI, WHR, non-fasting plasma glucose, plasma folate, creatinine and uric acid concentrations and eGFR were not related to feet ESC.

Multiple linear regression analysis was performed to investigate independent biological determinants of ESC. Lower ESC was associated with higher age and higher HbA1c ($p<0.05$, both) but not with gender, anthropometric and other biochemical parameters. Lower ESC was significantly associated both with increasing symptoms (MNSI A), ($p<0.05$) and increasing score on physical abnormalities suggestive of peripheral neuropathy (MNSI B), ($p<0.01$). Lower ESC was also significantly associated with increasing VPT measured by biothesiometer ($p<0.01$), and with higher number of abnormal CAN results ($p<0.05$).

Of the four CAN tests, lower feet ESC was associated with increasing postural fall in blood pressure (corresponding to sympathetic abnormality) ($p<0.05$), but not with other CAN tests. Patients with ESC<40 µS were more than 4 times likely to have 2 or more CAN test abnormal compared to patients with ESC>40 µS (OR 4.41 (1.72-11.29).

Correlation between VPT, MNSI and feet ESC was tested by simple linear regression analysis with prediction interval. VPT and MNSI were regressed on ESC and the predicted VPT and MNSI measurements were calculated for any observed value of ESC. Percentage of observations outside prediction interval was 2.6% for MNSI A, 1.5% for MNSI B and 4.5% for VPT, which indicates good correlation. Similar results were obtained for hands ESC.

The ability of feet ESC measurement to detect neuropathy against biothesiometer (VPT>20V) as measured by AUC was 0.70 (ROC curve). At 40 µS sensitivity was 0.50 and specificity was 0.78 and at 60 µS sensitivity was 0.75 and specificity 0.54.

Diagnosis Step 204

The method according to the invention allows assessing sudomotor function through evaluation of electrochemical skin conductance (ESC). In particular, feet electrochemical skin conductance appears very discriminative for sudomotor dysfunction diagnosis. A poor feet ESC can help identify patients with early small unmyelinated nerve-fibre dysfunction, and thus early autonomic neuropathy.

The results also show that the assessment of sudomotor dysfunction based on ESC through reverse iontophoresis is a quantitative reproducible method linked to cardiac autonomic neuropathies tests like Ewing tests and Heart Rate Variability analysis which is not influenced by glycaemia. In addition Foot ESC correlates with different degrees of peripheral sensory neuropathy, as estimated by VPT measurement and monofilament tests, and there is also progressive worsening of ESC measurements with increasing sensory perception threshold as estimated by VPT or monofilament results.

The association of sensory loss and sudomotor dysfunction as evaluated according to the present invention is also indicative of foot ulcer risk. Finally, evaluation of ESC is a simple and quick method, which does not require highly trained personnel.

What is claimed is:

1. A method for assessing sudomotor function of a patient, with a view to diagnosing autonomic neuropathy, the method being performed in a system comprising:

an anode and a cathode, intended to be placed on different regions of the patient body;

an adjustable DC source, which is controlled in order to feed the anode with a DC current;

the method comprising the following steps:

applying DC voltage pulses of varying voltage values in order to stress sweat glands, the voltage pulses lasting given durations allowing the stabilization of electrochemical phenomena in the body in the vicinity of the electrodes;

collecting data representative of the current between the anode and the cathode, and of the potential generated on the cathode through reverse iontophoresis for the different DC voltages;

from the data, computing results representative of the electrochemical skin conductance of the patient; and reconciling the data representative of the electrochemical skin conductance of the patient with reference data obtained in the same conditions on patients identified as suffering or not from autonomic neuropathy, and identifying the patient as suffering or not from sudomotor dysfunction.

2. The method according to claim 1, wherein the patient is identified as suffering from diabetes, and the reconciliation step allows identifying the patient as suffering or not from diabetes polyneuropathy.

3. The method according to claim 1, wherein the voltage values of the pulses are lower than 10 V.

4. The method according to claim 3, wherein the voltage values of the pulses are increased or decreased stepwise.

5. The method according to claim 1, wherein the electrodes include hands and feet electrodes.

6. The method according to claim 5, wherein the electrodes cover substantially all the surface of the hand palms and feet soles of the patient.

7. The method according to claim 1, wherein the computation step comprises the computation of electrochemical skin conductance values at given voltages, by computing the ratio between the current generated through the anode and the cathode, and the resulting voltage drop between anode and cathode.

8. The method according to claims 7, wherein the reconciling step comprises comparing the electrochemical skin conductance values of the patient at given voltages to predetermined thresholds.

9. The method according to claim 8, wherein the result of the comparison allows assessing the severity of sudomotor dysfunction.

10. The method according to claim 1, wherein the method further comprises at least one test among the following: peripheral vibration sensation through evaluation of the vibration perception threshold, cardiac autonomic neuropathy (CAN) assessment, neuropathy assessment through Michigan neuropathy screening instrument (MNSI).

11. The method according to claim 10, wherein the computed electrochemical skin conductance values are reconciled with the at least one other measurement, as a co-indicator of sudomotor dysfunction and diabetic polyneuropathy severity.

12. The method according to claim 11, comprising determining severe sudomotor dysfunction by low feet electrochemical skin conductance values in correlation with high sensory perception threshold as assessed by vibration perception threshold evaluation.

13. The method according to claim 11, comprising determining severe peripheral neuropathy by low feet electrochemical skin conductance values in correlation with high number of abnormal CAN results.

14. The method according to claim 11, comprising determining severe peripheral neuropathy by low feet electrochemical skin conductance values in correlation with increasing symptoms and score of physical abnormalities assessed by MNSI.

* * * * *